US008470346B2

(12) United States Patent
Chen (10) Patent No.: US 8,470,346 B2
(45) Date of Patent: *Jun. 25, 2013

(54) ANTI-VIRAL PHARMACEUTICAL COMPOSITIONS

(75) Inventor: Andrew Xian Chen, San Diego, CA (US)

(73) Assignee: Mast Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/111,873

(22) Filed: May 19, 2011

(65) Prior Publication Data

US 2011/0223259 A1    Sep. 15, 2011

Related U.S. Application Data

(63) Continuation of application No. 11/003,302, filed on Dec. 3, 2004, now Pat. No. 7,968,122.

(60) Provisional application No. 60/528,843, filed on Dec. 10, 2003.

(51) Int. Cl.
*A61K 9/00* (2006.01)

(52) U.S. Cl.
USPC ......................................................... 424/400

(58) Field of Classification Search
None
See application file for complete search history.

(56) References Cited

U.S. PATENT DOCUMENTS

| | | | |
|---|---|---|---|
| 3,404,987 A | 10/1968 | Kooistra et al. | |
| 4,465,666 A | 8/1984 | Lukas et al. | |
| 4,503,070 A | 3/1985 | Eby, III | |
| 4,548,950 A | 10/1985 | Baxendale et al. | |
| 4,661,354 A | 4/1987 | Finnerty | |
| 4,956,385 A | 9/1990 | Eby, III | |
| 5,100,879 A | 3/1992 | Ueno et al. | |
| 5,629,011 A | 5/1997 | Illum | |
| 5,711,938 A | 1/1998 | Larm | |
| 5,798,391 A | 8/1998 | Lagny et al. | |
| 6,080,783 A | 6/2000 | Davidson et al. | |
| 6,139,864 A | 10/2000 | Dürr et al. | |
| 6,207,653 B1 | 3/2001 | Larm et al. | |
| 6,231,889 B1 | 5/2001 | Richardson et al. | |
| 6,274,609 B1 * | 8/2001 | Yasueda et al. | 514/382 |
| 6,284,289 B1 | 9/2001 | Van den Berghe | |
| 6,321,750 B1 | 11/2001 | Kelly | |
| 6,391,318 B1 | 5/2002 | Illum et al. | |

(Continued)

FOREIGN PATENT DOCUMENTS

| | | |
|---|---|---|
| CN | 1457797 | 11/2003 |
| EP | 0012115 A1 | 6/1980 |

(Continued)

OTHER PUBLICATIONS

Contreras et al, HIV Latency: Present Knowledge and Future Directions, 2006, 1(6), 733-745.*

(Continued)

*Primary Examiner* — Paul Dickinson
(74) *Attorney, Agent, or Firm* — Kilpatrick Townsend & Stockton LLP (57) ABSTRACT

The present invention provides antiviral compositions that comprise one or more of an ionic multivalent metal component, a cationic polymer, and a cationic surfactant. The present invention also provides methods for making and using such antiviral compositions.

16 Claims, 6 Drawing Sheets

| No anti viral agent added (Positive control) | Zinc chloride only | Zinc chloride + Chitosan hydrochloride + Benzalkonium chloride |
|---|---|---|

U.S. PATENT DOCUMENTS

| | | |
|---|---|---|
| 6,423,329 B1 | 7/2002 | Sine et al. |
| 6,428,814 B1 | 8/2002 | Bosch et al. |
| 6,455,061 B2 | 9/2002 | Richardson et al. |
| 6,534,065 B1 | 3/2003 | Makin et al. |
| 6,570,054 B1 | 5/2003 | Gatto et al. |
| 6,632,445 B2 | 10/2003 | Richardson et al. |
| 7,163,720 B1 | 1/2007 | Dhaler et al. |
| 2002/0022660 A1 | 2/2002 | Jampani et al. |
| 2002/0136768 A1 | 9/2002 | Staats |
| 2002/0151521 A1 | 10/2002 | Burke et al. |
| 2003/0133993 A1 | 7/2003 | Hutcheson et al. |
| 2003/0206958 A1 | 11/2003 | Cattaneo et al. |
| 2004/0033260 A1 | 2/2004 | Rennie et al. |
| 2004/0057996 A1 | 3/2004 | Takada et al. |
| 2004/0072733 A1 | 4/2004 | Killam |
| 2004/0102429 A1 | 5/2004 | Modak et al. |

FOREIGN PATENT DOCUMENTS

| | | |
|---|---|---|
| EP | 0 692 253 A1 | 1/1996 |
| EP | 0692253 A1 | 1/1996 |
| JP | 01/11420 | 12/2001 |
| SE | 508760 | 11/1998 |
| WO | WO 95/28158 A1 | 10/1995 |
| WO | WO 96/41643 | 12/1996 |
| WO | WO 00/15192 A1 | 3/2000 |
| WO | PCT/JP 01/11420 | 12/2001 |
| WO | WO 03/060003 A1 | 7/2003 |
| WO | WO 2004/039379 | 5/2004 |
| WO | WO 2004/080210 A1 | 9/2004 |

OTHER PUBLICATIONS

Akihama, S. and Toyoshima, S., "Antiviral Effect of Zinc Complexes on Japanese B Encephalitis Virus," *Chemical & Pharmaceutical Bulletin*, 10(12):1254-1261, Aug. 1962.

Arnberg, N. et al., "Adenovirus Type 37 Binds to Cell Surface Sialic Acid Through a Charge-Dependent Interaction," *Virology*, 302(1):33-43, Oct. 10, 2002.

Bossche, G. V., "Alteration of viral infectious behavior by surface active agents," *Microbiol. Res.*, 149(2):105-114, Jun. 1994.

Chandy et al., "Effect of liposome-albumin coatings on ferric ion retention and release from chitosan beads," *Biomaterials* 17:61-66, 1996.

Chandy, T. and Sharma, C. P., "Effect of liposome-albumin coatings on ferric ion retention and release from chitosan beads," *Biomaterials*, 17(1):61-66, 1996.

Geist, F. C. et al., "In Vitro Activity of Zinc Salts against Human Rhinoviruses," *Antimicrobial Agents and Chemotherapy*, 31(4):622-624, Apr. 1987.

Hughs, M.P. et al., Measuring the dielectric properties of herpes simplex virus type 1 virions (with dielectrophoresis, *Biochimica et Biophysica Acta*, 1571(1):1-8, May 10, 2002.

In-Pharma Technologist.com, "West Pharma plans drug delivery exit," *West Pharmaceutical Services of the U.S.*, Jan. 7, 2004, URL http://www.in-pharmatechnologist.com/news/printNewsBis.asp?id=53243, download date Jun. 1, 2005.

Novick, S.G. et al., "How Does Zinc Modify the Common Cold? Clinical Observations and Implications Regarding Mechanisms of Action," *Medical Hypotheses*, 46(3):295-302, Mar. 1996.

Rabea et al., "Chitosan as Antimicrobial Agent: Applications and Mode of Action," *Biomacromolecules* 4(6):1457-1465, Nov./Dec. 2003.

Rabea, E. I. et al., "Chitosan as Antimicrobial Agent: Applications and Mode of Action," *American Chemical Society*, 4(6):1457-1465, Nov./Dec. 2003.

Varadinova, T. L. et al., "Mode of Action of Zn-Complexes on Herpes Simplex Virus Type 1 Infection In Vitro," *Journal of Chemometrics*, 5(1):3-9, 1993.

West Pharmaceutical Services, "Nasal Delivery," URL http://www.westpharma.com/drug%20delivery/nasal_delivery.asp, download date Sep. 14, 2004.

West Pharmaceutical Services, "Vaccine Delivery," URL http://www.westpharma.com/drug%20delivery/vaccine_delivery.asp, download date Sep. 14, 2004.

Yang et al., "Herpetic Simplex Keratitis and Trace Element Zinc," *Chinese Ophthalmic Research* 8(4):204-205, 1990.

Zai et al., "A Model of Hepadnavirus Infection and its Use in Anti-Infective Research," *Disease Surveillance* 10:383-385, 2002. (Cited Reference D5 at pp. 5-6, Office Action dated Sep. 12, 2008).

* cited by examiner

ANTI-VIRAL PHARMACEUTICAL COMPOSITIONS

CROSS-REFERENCE TO RELATED APPLICATIONS

This application is a continuation of U.S. patent application Ser. No. 11/003,302, filed Dec. 3, 2004, which application claims the benefit of U.S. Provisional Patent Application No. 60/528,843, filed Dec. 10, 2003, each of which is incorporated herein by reference in their entirety.

BACKGROUND OF THE INVENTION

1. Field of the Invention

The present invention relates generally to anti-viral agents. More particularly, the present invention relates to pharmaceutical compositions that are generally characterized as safe, substantially non-irritating and of broad-spectrum antiviral activities.

2. Description of the Related Art

The upper respiratory tract (URT) and genitalia are the routes most often used by viruses that led to viral infection. Viral infections in URT are best characterized by flu and common cold, and viral infections in genital areas are represented by herpes simplex infections, HIV infections, and other sexually transmitted diseases including hepatitis and those caused by Epstein-Barr viruses.

Until the advent of AIDS, flu or influenza virus was the last uncontrolled pandemic killer of humans. In the United States, influenza currently causes more morbidity and mortality than AIDS. For the 1990-1991 through 1998-1999 seasons, the greatest mean number of deaths was associated with influenza A virus, with annual mean (SD) of 8097 (3084) underlying pneumonia and influenza deaths (Thompson et *JAMA* 289:179-86, 2003).

Usually, the influenza viruses are a group of RNA viruses designated as types A, B, and C, with influenza A virus being the most virulent. This is because influenza A virus undergoes periodic antigenic shifts to evade the human immune systems and to promote widespread infection.

The influenza virus initially infects epithelial cells in the URT. It enters the host cells by a process of membrane fusion. This may occur at the cell plasma membrane or within the endocytic vacoular system. Upon binding to cell surface sialic acid residues on glycoproteins and glycolipids, the virus undergoes endocytosis via coated pits and vesicles and is then delivered to endosomes.

Four currently licensed agents are available in the United States for the systemic prophylaxis or treatment of the influenza virus: amantadine (SYMMETREL®) for the prophylaxis or treatment influenza A, rimantadine (FLUMADINE®) for prophylaxis or treatment influenza A in children, zanamivir (RELENZA®) for treatment of influenza A and B infection, and oseltamivir (TAMIFLU®) for treatment of influenza. None of the four antiviral agents has been demonstrated to be effective as a broad-spectrum anti-viral agent in preventing non-influenza viral infections or serious influenza-related complications (e.g., bacterial or viral pneumonia or exacerbation of chronic diseases). Worse still, the systemic application of these antiviral agents resulted in undesirable effects such as those related to CNS (e.g., nervousness, anxiety, difficulty concentrating, and lightheadedness) and gastrointestinal tract irritation. Accordingly, there is a need for a safe, non-irritating and of broad-spectrum anti-viral composition, which comprise ingredients that are pharmaceutically acceptable and safe.

The common cold is one of the most frequently occurring human illnesses and is responsible for substantial morbidity. The common cold is believed to be caused by rhinoviruses (RVs), and to a less extent, adenovirus. Rhinoviruses are nonenveloped viruses that contain a single-strand ribonucleic acid (RNA) genome. RVs belong to the Picornaviridae family, which includes the genera Enterovirus (polioviruses, coxsackieviruses groups A and B, echoviruses, numbered enteroviruses) and Hepatovirus (hepatitis A virus). Approximately 101 serotypes are identified currently.

RV can be transmitted by aerosol or direct contact. Primary site of inoculation is the nasal mucosa, although the conjunctiva may be involved to a lesser extent. RV attaches to respiratory epithelium and spreads locally. The major human RV receptor is intercellular adhesion molecule-1 (ICAM-1), which is involved in the natural response of the human defense system to injury by, for example, aiding in the binding between endothelial cells and leukocytes. RV takes advantage of the ICAM-1 by using it as a receptor for attachment. In addition, RV uses ICAM-1 for subsequent viral uncoating during cell invasion. Some RV serotypes also upregulate the ICAM-1 expression on human epithelial cells to increase infection susceptibility.

RV can directly cause or indirectly predispose an individual to a variety of upper respiratory tract infections (URTI) and lower respiratory tract infections (LRTI), which are less common.

Symptomatic treatment with analgesics, decongestants, antihistamines, and antitussives is currently the mainstay of therapy for RV-caused viral infections. Some clinicians advocate supplementation with vitamin C; however, high doses of vitamin C in children are not recommended. Zinc lozenges are not practical because of the metallic taste. The investigational agent, pleconaril (PICOVIR™), was found to be effective in inhibiting RV replication, but has not been approved for use. No effective drugs have been approved for the prophylaxis or treatment of the common cold.

The common viruses that are known to cause URT infections are listed in the table below:

| Viruses That Cause influenza-like illness | Viruses Causing Other Upper Respiratory Tract Infections |
| --- | --- |
| Influenzavirus A<br>Influenzavirus B | Rhinovirus<br>Adenovirus<br>Coronavirus<br>Parainfluenzavirus<br>Respiratory Syncytial Virus<br>Other Viruses |

In addition to the types of viruses discussed above, other types of deadly viral diseases that are transmitted through sexual contact such as the genital herpes and herpes simplex, are also of great concern regarding to their treatment. These diseases are caused by viruses called herpes simplex virus type 1 (HSV-1) and herpes simplex virus type 2 (HSV-2).

Herpes simplex viruses are complex by viral standards. They carry roughly 70,000 base pairs of double-stranded DNA. The DNA is enclosed within a capsid made of protein molecules, and the capsid is enclosed within an envelope made of a lipid bilayer. Protein molecules that help the virus bind to and infect certain types of cells project outwardly from the outer surface of the envelope. Those protein molecules are glycosylated, i.e., sugar molecules are attached to them, which makes it more difficult for an infected animal to generate an effective immune response to the virus.

Once contracted, genital herpes is incurable, and in addition to causing recurrent painful lesions, it poses a serious health threat. It can cause malignant transformation in animal and human cells, and has been linked to increased risks of cervical and vulvar cancer in women. The virus can also infect babies during birth, causing neonatal herpes, which is often fatal and can cause blindness, retardation, and other severe and permanent health problems if the baby survives.

Genital herpes is also believed to play an important role in the transmission of other sexually transmitted viruses, including acquired immunodeficiency syndrome (AIDS, which is caused by the human immunodeficiency virus, HIV). In effect, herpes lesions act as wounds or breaches in the protective layers of the skin and mucosal membranes, which provide vulnerable entry sites for invading viruses. If someone with genital herpes has intercourse with someone else who has HIV or some other sexually transmitted virus, the person with herpes is more likely than a non-herpetic individual would be to contract AIDS or another disease as a result. In addition, in people infected with both herpes and the HIV virus, herpes lesions presumably can increase the number of infectious HIV viral particles emitted by the infected person, since white blood cells infected by the HIV virus are likely to be present in the fluid in the herpes lesions. Therefore, any method for preventing the spread of genital herpes can help slow down the spread of AIDS and other sexually transmitted viruses.

The need for ways to reduce the spread of herpes and AIDS are especially acute. Despite intensive effort, there has been little progress in developing successful and effective prevention method.

In light of these problems confronting the prevention and the treatment of upper respiratory tract infections, sexually transmitted diseases, or other types of viral infections, it can be seen that a need exists in the art for a pharmaceutical composition that is generally characterized as safe, non-irritating and of broad-spectrum antiviral activities.

BRIEF SUMMARY OF THE INVENTION

The present invention provides antiviral compositions and methods for making and using such compositions. The compositions of the present invention are generally safe, non-irritating, and of broad-spectrum antiviral activities.

In one aspect, the present invention provides an antiviral composition that comprises one, two or all of the components selected from the group consisting of an ionic multivalent metal component, a cationic polymer, and a cationic surfactant.

In certain embodiments, the composition of the present invention comprises an ionic multivalent metal component (e.g., an ionic zinc component and a water soluble ferric salt). Such a composition may further comprise a cationic polymer or a cationic surfactant. In certain embodiments, the composition may comprise an ionic zinc component, a cationic polymer and a cationic surfactant. In certain other embodiments, the composition may comprise a water soluble ferric salt, a cationic polymer and a cationic surfactant.

In certain embodiments, the composition of the present invention comprises a cationic polymer or a cationic surfactant. In certain other embodiments, the composition may comprise both a cationic polymer and a cationic surfactant.

In certain embodiments, the composition of the present invention comprises, consists essentially of, or consists of, an ionic multivalent metal component, a cationic polymer, a cationic surfactant, and water.

In certain embodiments, the composition of the present invention comprises, consists essentially of, or consists of, an ionic multivalent metal component, a cationic polymer, a cationic surfactant, a preservative, and water.

In certain embodiments, the multivalent metal component is an ionic zinc component (e.g., zinc chloride). In certain other embodiments, the multivalent metal component is a water soluble ferric salt.

In certain embodiments, the cationic polymer is chitosan.

In certain embodiments, the cationic surfactant is benzalkonium chloride.

In certain embodiments, the preservative is ethylene diamine-tetraacetic acid (EDTA) or a salt thereof.

In certain embodiments, the antiviral composition comprises a hydrochloric salt of zinc, chitosan, and benzalkonium.

In certain embodiments, the antiviral compositions of the present invention do not contain any active antiviral ingredient other than an ionic multivalent metal ingredient (e.g., an ionic zinc component), a cationic polymer (e.g., chitosan), or a cationic surfactant (benzalkonium chloride).

In certain embodiments, the antiviral composition may further comprise an anti-viral protein. In certain other embodiments, the antiviral composition does not comprise any anti-viral proteins.

In certain embodiments, the antiviral composition may further comprise a viral antigen. In certain other embodiments, the antiviral composition does not comprise any viral antigens.

In certain embodiments, each component in the antiviral compositions of the present invention has been previously used safely in local applications of pharmaceutical compositions.

In certain embodiments, the antiviral compositions of the present invention further comprise pharmaceutically acceptable excipients such as a pH adjusting agent, pH buffer, a viscosity modifier, an osmotic agent, flavor, sweetener, colorant, and adhesive.

In certain compositions of the present invention, the concentration of the ionic multivalent metal component (w/w) may be about 0.01% to about 20% (e.g., about 0.01%, 0.02%, 0.03%, 0.04%, or 0.05% to about 0.5%, 1%, 2%, 3%, 4%, 5%, 6%, 7%, 8%, 9%, 10%, 12%, 14%, 15%, 16%, 18% or 20%), the concentration of the cationic polymer component (w/w) may be about 0.001% to about 20% (e.g., about 0.001%, 0.005%, 0.01%, 0.02%, 0.03%, 0.04%, or 0.05% to about 1%, 2%, 3%, 4%, 5%, 6%, 7%, 8%, 9%, 10%, 12%, 14%, 15%, 16%, 18%, or 20%), and the concentration of the cationic surfactant component (w/w) may be about 0.001% to about 2% (e.g., about 0.001%, 0.002%, 0.004%, 0.005%, 0.006%, 0.008%, 0.01% to about 0.02%, 0.05%, 0.1%, 0.2%, 0.3%, 0.4%, 0.5%, 0.6%, 0.7%, 0.8%, 0.9%, 1%, 1.2%, 1.4%, 1.6%, 1.8%, or 2.0%). The above ranges and the other ranges disclosed in other portions of the present application may include any values therebetween.

The compositions may be formulated as a solution, gel, lotion, suspension, cream, ointment, or other formulation appropriate for local application for the treatment or prevention of viral infectious diseases.

The compositions of the present invention may be applied by spraying, rubbing, spreading, dropping, cleansing, rinsing, or soaking the site of intended treatment with the antiviral compositions.

The present invention also provides kits for ameliorating viral infection that comprise the antiviral compositions as described above. In certain embodiments, the antiviral composition is contained in a container or an applicator.

In another aspect, the present invention provides methods for ameliorating viral infection. Such methods comprise administering to a subject (e.g., a mammal including human) in need thereof the compositions of the present invention in an amount effective to ameliorate viral infection.

In certain embodiments, the viral infection is caused by a virus selected from the group consisting of influenzavirus, rhinovirus, adenovirus, coronavirus, parainfluenzavirus, respiratory syncytical virus, HIV and herpes virus.

In certain embodiments, the viral infection results in a common cold, flu, canker sores, or a sexually transmitted disease.

In certain embodiments, the antiviral compositions of the present invention are administered locally, such as to skin, oral membrane, nasal membrane or genital membrane.

In certain embodiments, the viral infection is in upper respiratory tract or genital area.

DETAILED DESCRIPTION OF THE INVENTION

Antiviral Compositions

The present invention provides antiviral compositions. "Anti-viral" refers to the capability of reducing the number of viral particles in an infected subject (e.g., a cell line, a person or an animal) and/or reducing the likelihood of a subject exposed to potentially infective viral particles to contract a viral disease. In other words, the number of viral particles that infect a subject, or the likelihood of a subject to be infected by viral particles, is statistically significantly reduced with the administration of an antiviral compound or composition compared to that without the administration of the antiviral compound or composition. In certain embodiments, the antiviral compound or composition inhibits or reduces the contact between the viral particles and the subject, and/or the replication or emission of the viral particles.

Although zinc ion was known for its anti-viral activity (see, U.S. Pat. Nos. 4,956,385 and 6,321,750) and numerous efforts have been put forth in applying this property in the attempt to treat various types of infectious diseases, such applications have not been proven to be very effective.

The present invention, in certain embodiments, provides compositions that comprise an ionic multivalent metal component (e.g., a zinc salt) in combination of a cationic surfactant (e.g., benzalkonnium ion) and a cationic polymer (e.g., chitosan). Such compositions possess superior anti-viral activity to the previously known zinc-containing formulations (e.g., those containing only zinc ion as their active ingredients).

In certain embodiments, the present invention also provides antiviral compositions that comprise a cationic polymer, a cationic surfactant, or both a cationic polymer and a cationic surfactant. In certain embodiments, the present invention also provides antiviral compositions that comprise a cationic polymer, a cationic surfactant, or both a cationic polymer and a cationic surfactant, but not a multivalent metal component such as zinc.

In certain embodiments, the antiviral compositions do not further comprise any active antiviral ingredient other than a cationic polymer, a cationic surfactant, or an ionic multivalent metal component.

An "active antiviral ingredient" refers to a compound that has an antiviral activity when administered individually or in combination of one or more other compounds that do not have any antiviral activity.

"Antiviral activity" refers to the capability of reducing the number of viral particles in an infected subject and/or reducing the likelihood of a subject exposed to potentially infective viral particles to contract a viral disease.

In certain embodiments, the compositions of the present invention comprise only components that have not been known as having antiviral activities, and thus were previously regarded as "inactive ingredients" or "pharmaceutical excipients."

"Inactive ingredients" refers to compounds that are included in antiviral compositions, but do not have antiviral activities.

"Pharmaceutical excipients" refers to compounds that are included in antiviral compositions, and are pharmaceutically acceptable, but are typically not used as an active antiviral ingredient.

"Pharmaceutically acceptable" refers to the property of a compound that within the scope of sound medical judgment, suitable for use in contact with the tissues of humans and lower animals without undue toxicity, irritation, allergic response, and the like.

In certain embodiments, the formulations of the present invention further comprise one or more antiviral proteins. In certain other embodiments, the formulations of the present invention do not comprise any antiviral protein. The term "antiviral protein" refers to a protein that has antiviral activity, such as intercellular adhesion molecule (ICAM-1).

In certain embodiments, the formulations of the present invention further comprise one or more viral antigens. In certain other embodiments, the formulations of the present invention do not comprise any viral antigens. The term "viral antigen" refers to a molecule that is capable of inducing an immune response specific to viral infections. Viral antigens include antigens that are present in or derived from a viral particle or proteins encoded by a viral nucleic acid. Exemplary viral antigens include, but are not limited to, influenza virus antigens (e.g., haemagglutinin and neuraminidase antigens), HIV antigens (e.g., GP-120, G-160), and other viral proteins.

In certain embodiments, the formulations of the present invention further comprise one or more active drugs that are intended for systemic absorption or effects (e.g., morphine). In certain other embodiments, the formulations of the present invention further comprise one or more active drugs that are intended for systemic absorption or effects (e.g., morphine).

In certain embodiments, the formulations of the present invention are safe, substantially non-irritating, and of a broad spectrum of antiviral activity. As used herein, "safe" refers to the property of a composition (or a compound) that is substantially free of systemic toxicity; "non-irritating" refers to the property of a composition (or a compound) that causes no or an acceptably low level reaction in the area of application; and "broad-spectrum anti-viral activity" refers to the ability of a composition (or a compound) to inhibit or reduce the infectivity of more than one strain type of virus.

Ionic Multivalent Metal Component

"Ionic multivalent metal component" of the present antiviral composition refers to any compound or composition that may release a multivalent metal cation. It may be a multivalent metal salt (including both organic salt and inorganic salt) or a composition comprising a non-salt multivalent metal compound and a solubilizing agent that causes the non-salt multivalent metal compound to release multivalent metal cations.

"Multivalent metal salt" refers to any multivalent metal compound that is soluble in water and releases free multivalent metal cations in quantities that are effective in treating or preventing at least one type of virus infection (in in vitro tests), when dissolved in an aqueous solution. Multivalent metal cations include, but are not limited to, $Mg^{++}$, $Co^{++}$, $Ca^{++}$, $Cu^{++}$, $Fe^{++}$, $Fe^{+++}$, $Ni^{++}$, $Ni^{+++}$, $Al^{++}$, $Mn^{++}$, $Mn^{+++}$, $Ti^{++}$, $Ti^{+++}$, $Mo^{++}$, and $Mo^{+++}$.

In certain embodiments, the ionic multivalent component may be an ionic zinc component. "Ionic zinc component" of the present antiviral composition refers to any compound or composition that may release zinc ion. It may be a zinc salt (including both organic salt and inorganic salt) or a composition comprising a non-salt zinc compound and a solubilizing agent that causes the non-salt zinc compound to release zinc ions.

"Zinc salt" refers to any compound that is soluble in water and releases free zinc ions ($Zn^{++}$) in quantities that are effective in ameliorating at least one type of virus infection, when dissolved in an aqueous solution.

All organic zinc salts are suitable candidates for use in the compositions of the present invention for anti-viral activity. These include, but are not limited to, zinc acetate, zinc propionate, zinc butyrate, zinc formate, zinc gluconate, zinc glycerate (dihydroxypropionate), zinc glycolate (hydroxyacetate), zinc lactate, zinc pyruvate, and zinc gallate. Another class of organic zinc salts that can be used if desired include salts that can be made from di-carboxylic acids (which have two carboxy groups on a single molecule), such as maleic acid, malonic acid, and succinic acid. The corresponding zinc salts are zinc maleate, zinc malonate, and zinc succinate. Other organic salt candidates that are less soluble in aqueous solution and/or have relatively high pK values include zinc salicylate, zinc citrate, zinc oleate, zinc benzoate, zinc laurate, zinc stearate, zinc valerate, and zinc tartrate.

Inorganic salts may also be used in the present invention. Such inorganic salts include, but are not limited to, zinc chloride, zinc sulfate, and other similar salts.

Compositions that release free zinc ions may also be used in the present antiviral compositions. For example, when a non-salt zinc compound (such as zinc oxide) is added to an antiviral composition of the present invention as disclosed herein, along with a solubilizing agent that weakens or otherwise alters the chemical bond(s) between the zinc and the covalently bound atom(s) in the compound, thereby causing release of significant quantities of free zinc ions from the zinc compound in the presence of the solubilizing agent, the net result is functionally equivalent to providing a zinc salt as a single initial ingredient. Accordingly, if a mixture of such reagents (i.e, a non-salt zinc compound plus a solubilizing gent) is added to the formulation compositions of the present invention as disclosed herein, such a combination is regarded as the addition of an ionic zinc component to the antiviral composition.

Cationic Polymer

"Cationic polymer" refers to any positively charged, pharmacologically acceptable molecule formed of repeating units (including homopolymers, co-polymers, and heteropolymers). Cationic polymers of the present invention may be linear, branched or crosslinked.

The cationic polymers used for the antiviral compositions as disclosed herein, include, but are not limited to: (1) the group of polyamino acids, such as poly-(D, L or DL)-lysine salts, poly-(D, L or DL)-arginine salts, and all other forms of poly-cationic amino acid salts; (2) the group of polyamines, such as polymethylamine, polyethylamine, poly-n-propylamine, poly-iso-propylamine, polyethanolamine, polymethyl ethanolamine, polyethyl ethanolamine, ethyl diethanolamine, dimethyl ethanolamine, polymorpholine, poly-N-methylmorpholine, poly-N-ethylmorpholine, and mixtures thereof; (3) the group of poly((meth)acrylic acid) based copolymers with cationic groups (i.e. primary, secondary, tertiary or quaternary amine) on the repeating monomer unit, such as poly(dimethyl-aminoethylmethacrylate) (commercially available as EUDRAGIT®E by Degussa), poly(acrylic acid-b-methyl methacrylate), poly(methyl methacrylate-b-sodium acrylate), poly(methacrylic acid-b-neopentyl mathacrylate), poly(t-butyl methacrylate-b-ethylene oxide), poly(methyl methacrylate-b-sodium methacrylate), poly(methyl methacrylate-b-N-methyl-4-vinyl pyridinium iodide), and poly(methyl methacrylate-b-N,N-dimethyl acrylamide; (4) the group of cationic exchange resins, such as the strong acid cationic styrene-DVD gel matrix (commercially available as Dowex G-26(H), Dow chemical), and the weak acid cationic polyacrylic macroporous matrix (commercially available as Dowex Mac-3, Dow Chemical); (5) the group of proteins or peptides, such as protamine; and (6) the group of polysaccharides, such as chitosan.

Chitosan, a cationic polysaccharide, is routinely obtained from partial deacetylation of chitin, which originates from shells of crustaceans (e.g., crabs and prawns) (Muzzarelli, Chitin. In: Muzzarelli, ed. *Natural chelating polyers: Alginic acid, chitin, and chotosan*. New YorK: Pergamon Press; p83-252, 1973). Chitosan has been used extensively in the healthcare and consumer fields. In the United States, it is sold as a food supplement and as an oral over-the-counter slimming aid. Worldwide, it is utilized for the clarification of waste water (Sandford et al., In: Yalpani, ed. *Industrial polysaccharides: Genetics engineering, structure/properties relations and applications*. Amsterdam: Elsevier Science; p363-76, 1987), detoxification of hazardous waste, clarification of beverages, production of fungicides, creation of contact lens coating, and the manufacture of wound-healing scaffolding materials.

Because of its net positive charge, large molecular weight, gelation and film-forming characteristics, chitosan has also been investigated as a pharmaceutical excipient. Recently, chitosan has been used, due to its bioadhesive properties, to enhance transmucosal absorption (ChiSys™, West Pharmaceutical Services, Inc.), especially for nasal delivery of polar drugs, including peptides and proteins. The interaction of chitosan positive charges with the negatively charged sialic acid residues of the mucin present in mucus makes chitosan a powerful bioadhesive. The present inventor is unaware of any previous reports on using chitosan alone as an antiviral agent.

Chitosan is degraded in vivo by a large number of enzymes, including lysozymes, chitinases and glycosaminidases to glucosamine and glucosamine oligomer compounds. Such compounds are already present in the human body, therefore are harmless and non-toxic.

Cationic Surfactant

"Cationic surfactant" refers to a positively charged compound capable of lowering the surface tension of a liquid.

The candidate cationic surfactants useful for the antiviral compositions of the present invention include, but are not limited to, those in the form of alkylamine salts and quaternary ammonium salts. Examples of such surfactants are coconut alkyl amine acetate, stearyl amine acetate, lauryl trimethyl ammonium chloride, stearyl trimethyl ammonium chloride, cetyl trimethyl ammonium chloride, di-stearyl dimethyl ammonium chloride, cetrimide, and alkylbenzyl dimethyl ammonium chloride (such as benzalkonium or benzethonium type preservative, disinfectant and fungicide).

In addition to alkylamine salts and quaternary ammonium salts, cationic lipids can also be employed in the formulation compositions as disclosed herein. Suitable cationic lipid species which may be combined with the composition of the invention include, but are not limited to, 1,2 bis(oleoyloxy)-3-(trimethylammonio) propane (DOTAP); N-[1,-(2,3-dioleoyloxy) propyl]-N,N,N-trimethyl ammonium chloride (DOTMA) or other N—(N,N-1-dialkoxy)-alklyl-N,N,N-trisubstituted ammonium surfactants; 1,2 dioleoyl-3-(4'-trimethylammonio) butanoyl-sn-glycerol (DOBT) or cholesterol (4'-trimethylammonia) butanoate (ChOTB) where the trimethylammonium group is connected via a butanoyl spacer arm to either the double chain (for DOTB) or cholesterol group (for ChOTB); DORI (DL-1,2-dioleoyl-3-dimethylaminopropyl-B-hydroxyethylammonium) or DORIE (DL-1,2-O-dioleoyl-3-dimethylaminopropyl-.beta.-hydroxyethylammonium) (DORIE) or analogs thereof as disclosed in WO 93/03709; 1,2-dioleoyl-3-succinyl-sn-glycerol choline ester (DOSC); cholesterol hemisuccinate ester (ChOSC); lipopolyamines such as doctadecylamidoglycylspermine (DOGS) and dipalmitoyl phosphatidyesthanolamidospermine (DPPES), cholesterol-3.beta.-carboxyamidoethylenetrimethylammonium iodide, 1-dimethylamino-3-trimethylammonio-DL-2-propyl-cholesterol carboxylate iodide, cholesterol-3.beta.-carboxyamidoethyleneamine, cholesterol-3.beta.-oxysuccinamidoethylenetrim-ethylammonium iodide, 1-dimethylamino-3-trimethylammonio-DL-2-propyl-cholesterol-3.beta.-oxysuccinate iodide, 2-[(2-trimethylammonio)-ethylmethylamino]ethyl-cholesterol-3.beta.-oxysuccinate iodide, 3.beta.[N—(N',N'-dimethylaminoethane)-carbamoyl]-cholesterol (DC-chol), and 3.beta.-[N-(polyethyleneimine)-carbamoyl]cholester.

Benzalkonium chloride (i.e., alkyldimethyl (phenylmethyl) ammonium chloride [CAS 8001-54-5]), or its closely relative compound benzethonium, is a surface-active germicide for many pathogenic nonsporulating bacteria and fungi. Aqueous solutions of this agent have a low surface tension, and possess detergent, keratolytic, and emulsifying properties that aid the penetration and wetting of tissue surfaces. Commercially, benzalkonium chloride has been widely used in ophthalmic, otic, nasal and injectable formulations, as well as in cosmetic products as preservatives. In addition, benzalkonium chloride has been used as spermicides, which are a type of contraceptive for birth control. Furthermore, benzalkonium chloride has been formulated into topical antisepsis (ZEPHIRAN®, Sanofi) for skin and mucous membranes and as a disinfectant in surgery, obstetrics and gynecology, urology, ophthalmology, otorhinolaryngology and general practice.

In general, benzalkonium chloride has mostly been indicated for topical applications. The present inventor is unaware of any previous reports on using benzalkonium alone as an antiviral agent.

Concentrations of Cationic Components

"Concentration by weight" or "w/w" refers to the ratio (in percentage) of the weight of a component (e.g., an ionic zinc component) of a composition (e.g., an antiviral composition) to the total weight of the composition, if not otherwise noted.

In certain embodiments, the ionic multivalent metal component (e.g., ionic zinc component or a water soluble ferric salt) is present in an amount (in chloride salt equivalent) from about 0.01% to about 20% of the total weight of a composition of the present invention, such as from about 0.01% to about 10%, from about 0.02% to about 5%, or from about 0.05% to about 0.5% of the total weight of a composition of the present invention.

In certain embodiments, the ionic zinc component is present in an amount (in chloride salt equivalent) at most about 0.1%, 0.2%, 0.3%, 0.4%, 0.5%, 0.6%, 0.7%, 0.8%, 0.9%, 1%, 1.2%, 1.4%, 1.6%, 1.8%, 2%, 2.2%, 2.4%, 2.6%, 2.8%, 3.0%, 3.5%, 4.0%, 4.5%, or 5% by weight.

In certain embodiments, the cationic polymer component is present in an amount (in chloride salt equivalent) from about 0.001% to about 20% of the total weight of a composition of the present invention, such as from about 0.001% to about 10%, from about 0.01% to about 5%, from about 0.1% to about 5%, or from about 0.05% to about 2% of the total weight of a composition of the present invention.

In certain embodiments, the cationic surfactant component is present in an amount from about 0.001% to about 2% of the total weight of a composition of the present invention, such as about from 0.001% to about 1%, from about 0.001% to about 0.1%, from about 0.01% to about 1%, or from about 0.002% to 0.02% of the total weight of a composition of the present invention.

Other Optional Components

The compositions of the present invention may optionally comprise one or more pharmaceutically useful excipients, including but not limited to, pH adjusting agents, pH buffer, viscosity modifiers, osmotic agents, flavor, sweetener, preservatives (e.g., metal chelators), adhesives and colorants. The selection and use of each agent are determined based on the practices known to those skilled in art. The common concentration for various excipients can be found in the "*Handbook of Pharmaceutical Excipients*" 3$^{rd}$ edition, ed. Kibbe, Ph.P. press.

An exemplary preservative is EDTA or its salts (disodium edetate). In certain embodiments, the concentration of disodium edetate may be about 0.001% to about 2% of the total weight of a composition of the present invention, such as about from 0.001% to about 1%, from about 0.001% to about 0.1%, or from about 0.05% to 0.1% of the total weight of a composition of the present invention.

Exemplary Antiviral Compositions of the present invention include, but are not limited to, the following compositions:

Antiviral Composition 1 (Same as the composition used in Example 1)

| Component | % by weight |
|---|---|
| Chitosan hydrochloride | 1.50% |
| Zinc chloride | 0.10% |
| Benzalkonium chloride | 0.02% |
| Water to add to | 100% |
| NaCl/HCl to adjust pH to | pH 4.5-6.5 |

Antiviral Composition 2

| Component | % by weight |
|---|---|
| Chitosan hydrochloride | 1.50% |
| Zinc chloride | 0.10% |
| Benzalkonium chloride | 0.02% |
| Disodium edetate | 0.10% |
| Water to add to | 100% |
| NaCl/HCl to adjust pH to | pH 4.5-6.5 |

Antiviral Composition 3

| Component | % by weight |
|---|---|
| Chitosan hydrochloride | 1.50% |
| Benzalkonium chloride | 0.02% |
| Water to add to | 100% |
| NaCl/HCl to adjust pH to | pH 4.5-6.5 |

Antiviral Composition 4

| Component | % by weight |
|---|---|
| Chitosan hydrochloride | 1.50% |
| Zinc chloride | 0.10% |
| Disodium edetate | 0.10% |
| Water to add to | 100% |
| NaCl/HCl to adjust pH to | pH 4.5-6.5 |

Antiviral Composition 5

| Component | % by weight |
|---|---|
| Zinc chloride | 0.10% |
| Benzalkonium chloride | 0.02% |
| Water to add to | 100% |
| NaCl/HCl to adjust pH to | pH 7.4 |

Antiviral Composition 6

| Component | % by weight |
|---|---|
| Chitosan glutamate | 1.50% |
| Zinc gluconate | 0.10% |
| Benzalkonium chloride | 0.02% |
| Water to add to | 100% |
| NaCl/HCl to adjust pH to | pH 4.5-6.5 |

Antiviral Composition 7

| Component | % by weight |
|---|---|
| Chitosan chloride | 1.50% |
| Ferric chloride | 0.10% |
| Benzalkonium chloride | 0.02% |
| Water to add to | 100% |
| NaCl/HCl to adjust pH to | pH 4.5-6.5 |

Antiviral Composition 8

| Component | % by weight |
|---|---|
| Chitosan chloride | 1.50% |
| Ferrous gluconate | 0.10% |
| Benzalkonium chloride | 0.02% |
| Water to add to | 100% |
| NaCl/HCl to adjust pH to | pH 4.5-6.5 |

Antiviral Composition 9

| Component | % by weight |
|---|---|
| EUDRAGIT ® E100* | 1.50% |
| Zinc chloride | 0.10% |
| Benzalkonium chloride | 0.02% |
| Water to add to | 100% |
| NaCl/HCl to adjust pH to | pH 5.5-6.5 |

*Poly(dimethyl-aminoethylmethacrylate, commercially available from Degussa

Antiviral Composition 10

| Component | % by weight |
|---|---|
| Dowex G-26(H)** | 1.50% |
| Zinc chloride | 0.10% |
| Benzalkonium chloride | 0.02% |
| Water to add to | 100% |
| NaCl/HCl to adjust pH to | pH 6.5-7.5 |

**Strong acid cationic styrene-DVD gel matrix commercially available from Dow chemical Antiviral Composition 11

| Component | % by weight |
|---|---|
| Chitosan chloride | 1.50% |
| Zinc chloride | 0.10% |
| Benzalkonium chloride | 0.02% |
| Sodium chloride | 0.27 |
| Water to add to | 100% |
| NaCl/HCl to adjust pH to | pH 5.6 |

Antiviral Composition 12

| Component | % by weight |
|---|---|
| EUDRAGIT ® E100 | 1.50% |
| Zinc chloride | 0.10% |
| Benzalkonium chloride | 0.02% |
| Sodium chloride | 0.27 |
| Water to add to | 100% |
| NaCl/HCl to adjust pH to | pH 6 |

Antiviral Composition 13

| Component | % by weight |
|---|---|
| Chitosan chloride | 0.15% |
| Zinc chloride | 0.10% |
| Benzalkonium chloride | 0.02% |
| Sodium chloride | 0.27 |
| Water to add to | 100% |
| NaCl/HCl to adjust pH to | pH 5.6 |

Antiviral Composition 14

| Component | % by weight |
|---|---|
| EUDRAGIT ® E100 | 0.15% |
| Zinc chloride | 0.10% |
| Benzalkonium chloride | 0.02% |
| Sodium chloride | 0.27 |
| Water to add to | 100% |
| NaCl/HCl to adjust pH to | pH 6.2 |

Antiviral Composition 15

| Component | % by weight |
|---|---|
| Chitosan chloride | 0.05% |
| Zinc chloride | 0.10% |
| Benzalkonium chloride | 0.02% |
| Sodium chloride | 0.27 |
| Water to add to | 100% |
| NaCl/HCl to adjust pH to | pH 5.6 |

Antiviral Composition 16

| Component | % by weight |
|---|---|
| Chitosan chloride | 0.15% |
| Zinc chloride | 0.10% |
| Benzalkonium chloride | 0.02% |
| Sodium chloride | 0.27 |
| Water to add to | 100% |
| NaCl/HCl to adjust pH to | pH 5.6 |

The compositions of the present invention may be generally prepared by first dissolving appropriate amounts of various components (e.g., ionic multivalent metal component, cationic polymer, and/or cationic surfactant) in water, optionally adjusting pH to facilitate the dissolution of the components, filtrating the solution with a filter with an appropriate membrane pore size, adjusting the pH to the target pH range if needed, and adding water to the final weight. The compositions may be further sterilized (e.g., by autoclaving), and stored in appropriated containers.

An exemplary method for preparing the antiviral compositions may include the following general steps:
1. Weigh out the ionic multivalent metal, cationic polymer, and/or cationic surfactant into a clean container,
2. Add purified water to 90% of the final weight, mix well to dissolve all components,
3. As needed, add hycrochloric acid solution to adjust the pH until all components are dissolved,
4. Filter the solution through a filter with membrane pore size rated at 0.8 to 1.2 micron,
5. Add sodium hydroxide and/or hydrochloric acid solution to the target pH range,
6. Add purified water to the final weight,
7. Autoclave the preparation at 121° C. for 20-30 minutes,
8. Fill into the final containers, such as nasal spray bottles.

Use of Antiviral Compositions

The present invention also provides a method for ameliorating viral infection comprising administering to a subject in need thereof the composition described herein in an amount effective to ameliorate viral infection. Ameliorating viral infection is understood to encompass (1) reducing or eliminating the likelihood that a person or an animal exposed to potentially infective viral particles will be infected with the viral particles, or (2) reducing or eliminating the progression of viral infection (e.g., reducing the number of viral particles in a host). A "subject in need thereof" may be a human or an animal (e.g., a mammal) that is at risk for developing viral infection (e.g., being exposed to potentially infective viral particles) or already has contracted a viral infection.

The compositions of the present invention may be administered to a subject locally. The term "local" encompasses application in and around the site of intended treatment, and excludes peroral, subcutaneous, intravenous and intramuscular administration that are categorized as systemic application. Exemplary local administration includes, but is not limited to: (1) "topical" application, including the treatment on the human skin, hair and nail; (2) "mucosal" application, including the treatment on the nasal mucous membrane, oral mucous membrane (also referred to as oral cavity), vaginal mucous membrane, or in general, the genitalia area; and (3) "ophthalmic" application, including the treatment in the eye.

The compositions of the present invention may be in any form suitable for local administration. For example, the composition may be in a form of a solution, paste, gel, suspension, lotion, cream, aerosol, dressing, bandage, lacquer, or ointment formulation for local application. In certain embodiments, the compositions of the present invention are formulated (or adapted) for preventing or treating virus infection through nasal passages, such as in a form of nasal ointments, nasal drops, nasal washes, nasal packings, or nasal sprays.

Any methods appropriate for local administering a pharmaceutical composition to a subject known in the art may be used in the present invention. Such methods generally cause the formulation to coat and remain in contact with those membranes or skin surfaces for a period of time, like a chemical barrier at those sites.

One exemplary method of applying an antiviral formulation of the present invention to the nasal mucus membrane, the oral cavity, or the genital surfaces involves removing a small quantity (such as several milliliters) of a solution, gel, suspension, lotion, cream, ointment, or similar formulation from a container, followed by spraying or by squeezing the container which is preset for a desired amount directly at the area(s) of interest, or by spreading the formulation across the mucus or skin area(s) with a finger or an applicator.

The compositions of the present invention may be used to ameliorate various viral infection such as infection of influenza virus A, influenza virus B, adenovirus, coronavirus, parainfluenzavirus, rhinovirus, respiratory syncytial virus, herpes simplex virus, HIV, etc. They may be useful in preventing, reducing the duration, or relieving, the symptoms of the common cold, flu, other respiratory viral infections, and sexually transmitted diseases.

In certain embodiments, the formulations disclosed herein may prevent the spreading of the severe acute respiratory syndrome (SARS). SARS is spread when someone with SARS coughs or sneezes droplets into the air and someone else inhales them. By forming a viscous membrane over nasal mucous and by deactivating viruses on contact, the formulation of the present invention could provide an effective means to prevent the virus from spreading. This formulation is particularly useful among people who are in close contact with SARS patients, healthcare workers or air travelers.

The effectiveness of a given antiviral composition according to the present invention may be evaluated using in vitro cultured virus-transfected cells (such as those described in the examples below). Alternatively, the effectiveness may be determined using in vivo animal models and/or patients. Such animal models and methods for measuring the effectiveness of an antiviral composition in animal models and/or patients are known in the art (see, e.g., Cheng et al., Retina 19: 325-31, 1999; Lee et al., *Pharm. Res.* 9: 979-89, 1992; Polas et al., *Antimicrob. Agents Chemother.* 34: 1414-21, 1990; Saito et al., *Ann. Neuro.* 15: 548-58, 1984; Birch et al, *J. Infect. Dis.* 162: 731-4, 1990).

EXAMPLES

The following examples are provided for the purposes of illustrating certain embodiments of the present invention and not by way of limitation of the scope of the present invention.

Example 1

The composition shown in Table 1.1 was comprised of 1.5% (w/w) chitosan hydrochloride salt, 0.1% (w/w) zinc chloride, 0.02% benzalkonium chloride, and 98.38% (w/w) water. The formulation of such composition was prepared by mixing all three of the cationic components in the aqueous phase (water) and stirring to dissolve them completely at room temperature. Since both zinc chloride and benzalkonium chloride were in the salt form, their dissolution process was rapid. As for chitosan, its solubilization process was gradual. The final formulation prepared was in a form of a gel.

TABLE 1.1

| Component | % by weight |
| --- | --- |
| Chitosan hydrochloride | 1.50% |
| Zinc chloride | 0.10% |
| Benzalkonium chloride | 0.02% |
| Water | 98.38% |
| | pH 4.5-6.5 |

Figure 1:
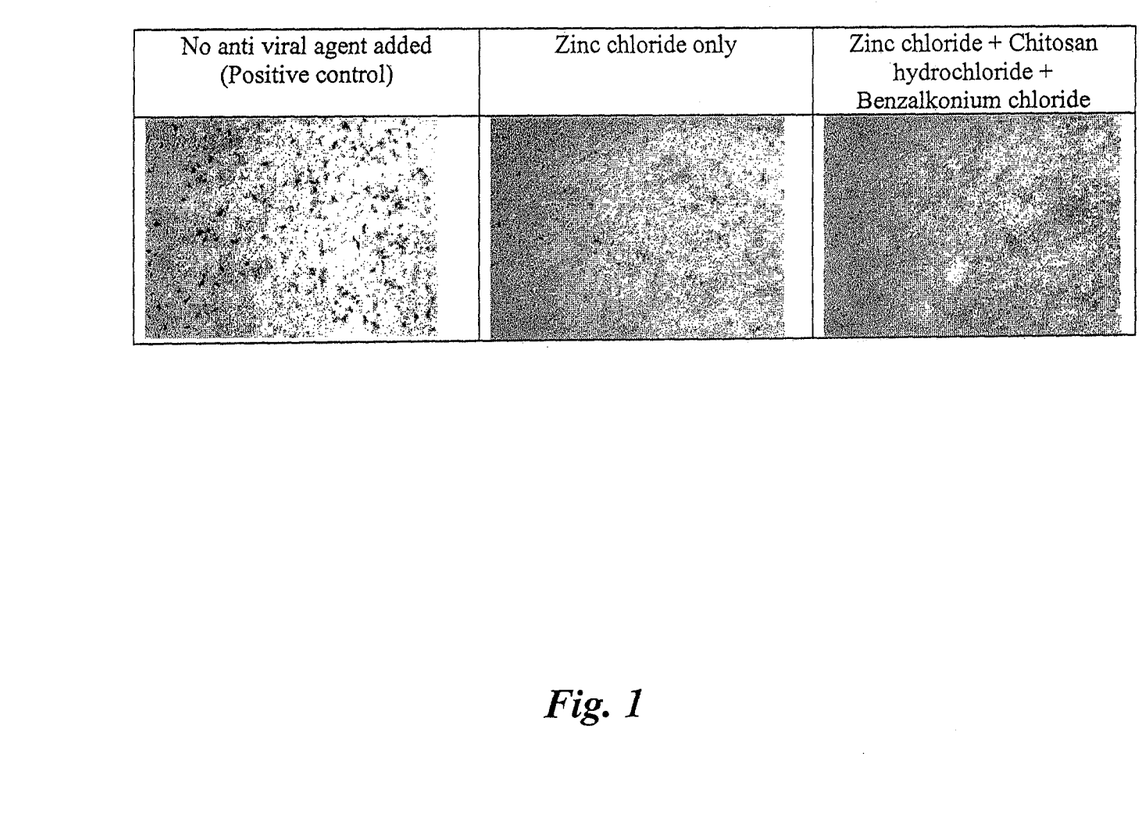
FIG. 1 are photographs of human embryonic kidney cells infected by Adenovirus carrying a beta galatosidase gene without any treatment (left panel), with the treatment of 0.1% zinc chloride (middle panel), and with the treatment of a composition of the present invention as described in Table 1.1. The virus-infected cells are blue due to x-gal staining.

The formulation in the form of a gel prepared in such a manner was tested in vitro for its effective anti-viral activity using adenovirus as the target virus. It was found that the gel exhibited a greatly increased anti-viral effect synergistically: The gel showed much stronger anti-viral activity compared to a composition that comprises zinc chloride alone at the same zinc concentration. The photographs presented in FIG. 1 represent human embryonic kidney cells infected by adenovirus carrying beta galactosidase gene. The cell culture media were treated with no additive (left panel), zinc chloride (middle panel), and the gel as prepared as described above (right panel). The gel was diluted twenty (20) times on weight basis prior to the treatment. As a result, the zinc chloride concentration applied was 0.005% by weight in the diluted form. The virus-infected cells are blue (from x-gal staining). The gel was highly effective in preventing adenovirus infection. In addition to adenovirus, the gel has also demonstrated similar in vitro inhibitory effect against herpes simplex type 1 virus.

Both zinc chloride and benzalkonium chloride disclosed herein for the formulation of the present invention have been listed as inactive ingredient for approved products by the U.S. Food and Drug Administration (FDA), indicating their good safety records for human use. Further, chitosan has been widely used in drug and food supplement products, as described above, for human consumption.

The gel formulation prepared herein is a viscous gel, which provides excellent muco-adhesiveness by forming a physical barrier over the mucous membrane for a prolonged period of time.

Example 2

Figure 2:
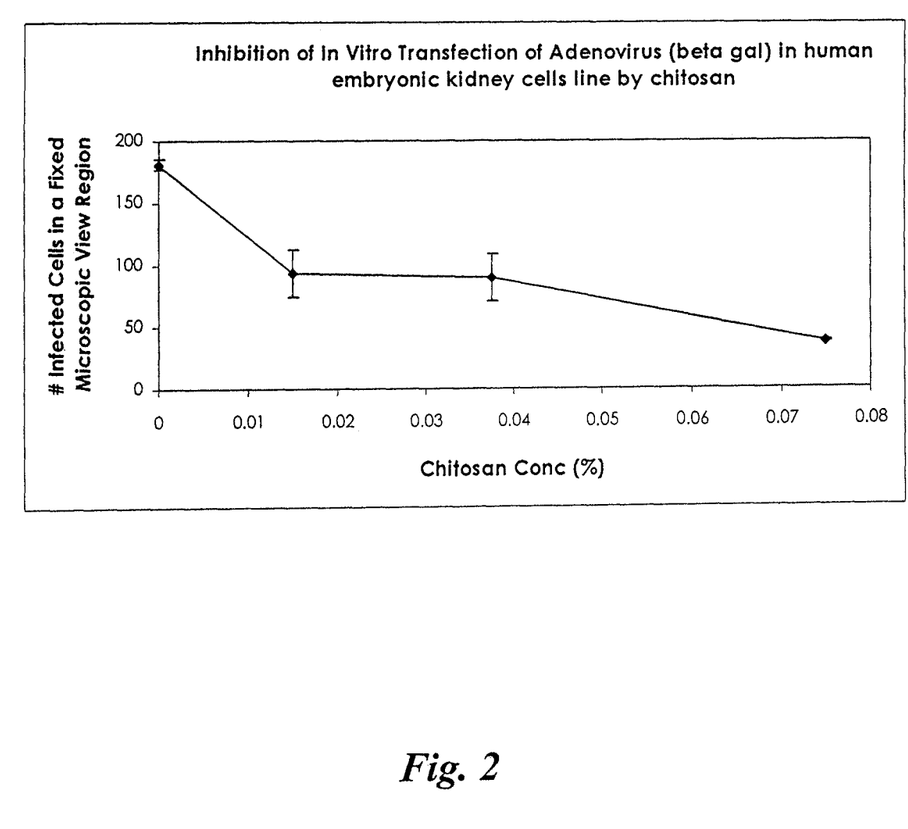
FIG. 2 depicts inhibition of in vitro transfection of Adenovirus (based on beta galactosidase activity of the virus that carries the gene encoding for the enzyme) in human embryonic kidney cell line by chitosan. The inhibition herein indicated the effectiveness of chitosan alone in demonstrating, to a certain extent, the anti-viral activity against the transfection of Adenovirus in vitro.

A formulation in the form of a gel was prepared (in a similar manner as described in Example 1) using only chitosan and was tested in vitro for its effective anti-viral activity using adenovirus carrying beta galactosidase gene as the target virus in human embryonic kidney cell line. The concentration of chitosan was 1.5% (w/w) with 98.5% water (w/w) in the formulation. Before applying such a gel formulation to the cell line culture, the gel formulation was diluted to obtain three chitosan concentrations of 0.015%, 0.0375%, and 0.075% (w/w) prior to treating the infected human embryonic kidney cells in the cell culture medium. A blank control (no chitosan added) was used for comparison. The results, summarized as the number of infected cells in a fixed microscopic view region as a function of chitosan concentration, are presented in FIG. 2.

The results show that chitosan alone possessed certain level of anti-viral activity; the number of infected cells decreased with the increase in chitosan concentration.

Example 3

A series of formulations were prepared (in a similar manner as described in Example 1) with various combinations of zinc chloride, chitosan, benzalkonium chloride and disodium edetate as preservatives. The formulations were tested in vitro for its effective anti-viral activity using adenovirus (beta galactosidase) as the target virus in human embryonic kidney cell line. A blank control (no anti-viral agent added) was used for comparison. For the formulations containing chitosan, its concentration was 1.5% (w/w). Before applying the formulations to the infected human embryonic kidney cell line culture, those formulations containing chitosan were diluted to obtain a chitosan concentration of 0.075% (w/w), which was found to be the most effective concentration in inhibiting adenovirus infection in Example 2. Others were diluted by 20 times before application. The formulation designs were given Table 3.1.

TABLE 3.1

| Components | Formulation (%, w/w) | | | | | | | | | |
| --- | --- | --- | --- | --- | --- | --- | --- | --- | --- | --- |
| | 1 | 2 | 3 | 4 | 5 | 6 | 7 | 8 | 9 | C |
| Chitosan | 1.5 | 1.5 | 1.5 | 1.5 | 1.5 | — | — | — | — | — |
| Zinc chloride | — | 0.1 | — | — | 0.1 | 0.1 | — | — | 0.1 | — |
| Benzalkonium | — | — | 0.02 | — | 0.02 | — | 0.02 | — | 0.02 | — |
| Disodium | — | — | — | 0.1 | 0.1 | — | — | 0.1 | 0.1 | — |
| Purified | 98.5 | 98.4 | 98.48 | 98.4 | 98.28 | 99.9 | 99.98 | 99.9 | 99.78 | 100 |

Figure 3:
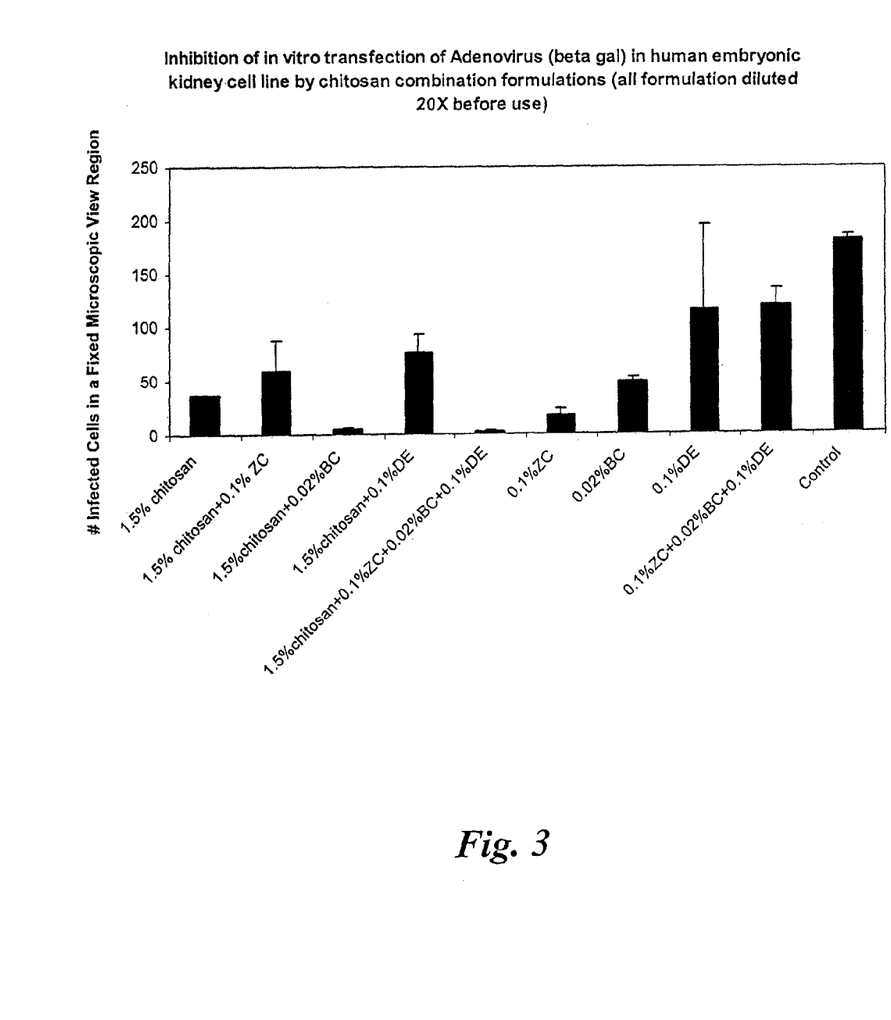
FIG. 3 shows inhibition of in vitro transfection of Adenovirus (based on beta galactosidase activity of the virus that carries the gene encoding for the enzyme) in human embryonic kidney cell line by chitosan combination formulations. All formulations were diluted 20 times before use.

The results, summarized as the average number of infected cells in a fixed microscopic view region as a function of the formulation applied, are presented in Table 3.2 and graphically in FIG. 3.

From Table 3.2, it can be seen that the synergistic ability of the combination of zinc chloride (ZC), benzalkonium chloride (BC) and chitosan in formulation 5 was the most effective in inhibiting the adenovirus, comparing with the effect generated by zinc chloride alone (formulation 6) and other combinations.

TABLE 3.2

| Formulation | Components | Average Number of Infected Cells in a Microscopic Viewing Area |
| --- | --- | --- |
| 1 | 1.5% chitosan | 37.5 |
| 2 | 1.5% chitosan + 0.1% ZC | 60 |
| 3 | 1.5% chitosan + 0.02% BC | 5.5 |
| 4 | 1.5% chitosan + 0.1% DE | 77.5 |
| 5 | 1.5% chitosan + 0.1% ZC + 0.02% BC + 0.1% DE | 3 |
| 6 | 0.1% ZC | 18 |
| 7 | 0.02% BC | 49.5 |
| 8 | 0.1% DE | 116.5 |
| 9 | 0.1% ZC + 0.02% BC + 0.1% DE | 119.5 |
| Control | None added | 181.5 |

Example 4

This example shows that exemplary antiviral formulations of the present invention are effective against rhinovirus and influenza B virus infections in in vitro cell protection assays.

The objective of this study was to evaluate in vitro cell protection efficacy against rhinovirus and influenza B virus infections by two antiviral compositions of this invention in comparison to a zinc-only preparation.

Two antiviral compositions of this invention (Antiviral Formulation I and Antiviral Formulation II) and a zinc-only preparation were provided as sterile solutions. The compositions of these three preparations are as follow:

Test Article Compositions

| % w/w | Antiviral Formulation I (Same as the Antiviral Composition 11) | Antiviral Formulation II (Same as the Antiviral Composition 12) | Zinc-only |
|---|---|---|---|
| Chitosan chloride (Chimarin ® M-010 by Carmeda AB, Sweden) | 1.5 | | |
| Zinc chloride, USP | 0.1 | 0.1 | 0.1 |
| Benzalkonium chloride, SigmaUltra | 0.02 | 0.02 | |
| Sodium chloride, USP | 0.27 | 0.27 | |
| EUDRAGIT ® E100 | | 1.5 | |
| NaCl/HCl to adjust pH | 5.6 | 6.25 | 6.0 |
| Di-ionized water to QS | 100 | 100 | 100 |

Human H1-Hela cell line (Catalog# CRL-1958) and MDCK cell line (Catalog# CCL-34) were purchased from ATCC (Manassas, Va.). Human Rhinovirus type 15 (Catalog# VR-285) and Influenza B virus (Catalog# VR-1535) were purchased from ATCC (Manassas, Va.). All cell culture reagents were purchased from GIBCO/Invitrogen.

For cell culture, H1-HeLa cells were maintained in DMEM with 10% FBS, while MDCK cells in advanced MEM with 2% FBS. Both cell lines were cultured at 37° C., with 5% $CO_2$ and 100% humidity.

For virus propagation, the rhinoviruses were amplified to high titer by successive infection of the target H1-hela cells. Viral infection was initiated in culture medium supplemented with 20 mM HEPES (pH 7.4)-10 mM $MgCl_2$. After 48 h of infection at 35° C., viruses were released from the cells by three freeze-thaw cycles at −80° C. and 37° C. The cell debris was discarded, while the supernatant containing the amplified rhinoviruses was aliquoted and frozen at −80° C.

Influenza B viruses were propagated by infection of the adapted MDCK cells. Viral infection was conducted in serum-free MEM medium supplemented with 10 mM HEPES (pH 7.4), 2 mM Glutamine, 0.15% BSA and 2 ug/ml TPCK-treated trypsin. After 48 h of infection at 35° C., viruses were released from the cells by three freeze-thaw cycles at −80° C. and 37° C. The cell debris was discarded, while the supernatant containing the amplified Influenza B viruses was aliquoted and frozen at −80° C.

To examine protection activity of Antiviral Formulations I and II against viral infection, the levels of cell death due to rhinovirus virus infection were compared to these of positive and negative controls as well as to that of uninfected cells after pretreatment of viral lysates with variuos concentrations of either formulation.

In a typical assay, H1-Hela cells were seeded into 24-well plates 18 h before an assay at 70-80% cell confluency. Viral lysate was mixed with equal volume of undiluted, various diluted Formulation or positive control solutions using PBS as a diluent reagent.

The mixtures were incubated at room temperature for 30 min, then added onto cells which were washed once with PBS after removal of the culture medium from each well, in triplicate wells (n=3). The final concentrations of each Antiviral Formulations or the zinc-only preparation in the wells were at ½, ¼ and ⅛ of the orignial strength.

The infection was allowed to proceed for 48 h at 35° C. The remaining viable cells in wells were stained with 0.5% crystal violet in 20% methanol for 5 min at room temperature, and were washed extensively with water after staining.

This staining method was used to differentiate the viable cells and virus-infected cells. Virus-infected cells or the dead cells are not strained by this method (the wells remained colorless) while the wells containing viable cells or the protected cells are stained blue. Color images for the stained wells of each plate were recorded using Sony digital camera.

Cell protection assays were performed in the same way with MDCK cells using Influenza B virus, except the virus lysate supplemented with fresh 1 μg/mlTPCK-treated trypsin.

Figure 4:
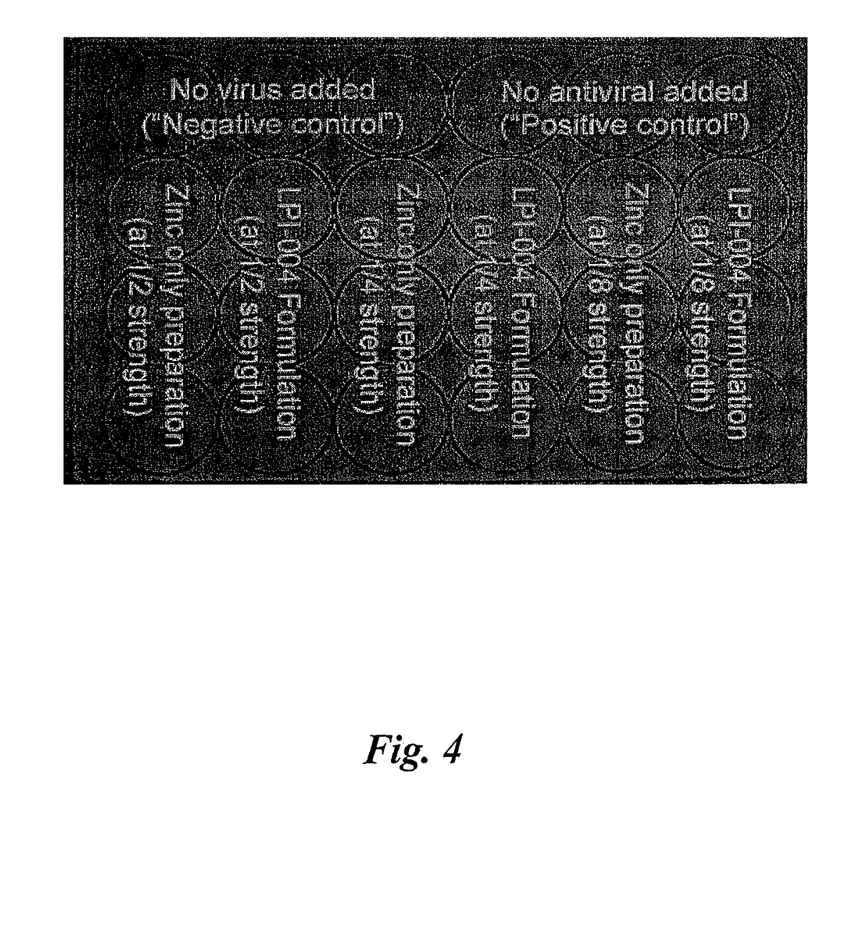
FIG. 4 illustrates anti-viral assays conducted using exemplary anti-viral formulations. Cells were split the day prior to an assay in triplicate wells for each testing sample. Following the mixing of the testing samples and virus, cells were kept at 35° C. for 48 h. "Negative control" wells: no virus was added. "Positive control" wells: viruses were added without any anti-viral reagent. "Zinc only preparation" wells: contains ionic zinc similar to the Zicam® composition. At the full strength, the zinc ion concentration is 0.048%. "LPI-004 formulation": also contains zinc ion at the same concentration as in the "Zinc only preparation". "Antiviral Formulation 1" and "Antiviral Formulation 2" differ by their cationic polymers.

FIG. 4 shows the layout of each well plate. In each plate, three wells in a row at upper left corner were used as the "No virus added" or "Negative control", in which the cells were grown healthy and were not infected with virus. The three wells in a row at the upper right corner were reserved as the "No antiviral added" or "Positive control" in which the cells were infected with virus and no antiviral formulation or zinc-only preparation was added to protect the cells. The virus infected and antiviral added wells were arranged vertically ("column") under the row of the negative and positive control wells. Each column of 3 wells represents one test article at a specified strength.

Figure 5A:
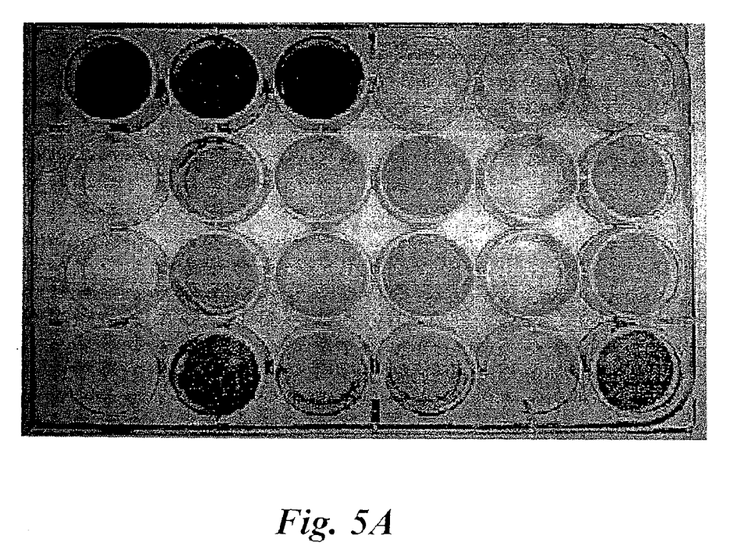
FIG. 5 shows cell protection assay against Influenza B virus. Blue color represents protected cells stained by crystal violet dye. The absence of blue color indicates that all cells were infected and killed by the virus. For Panel A, Antiviral Formulation 1 was used; panel B same as panel A except Antiviral Formulation 2 was used. Both Antiviral Formulation 1 and Antiviral Formulation 2 were able to completely protect the cells from viral infection, even at ⅛ of their original strength. In contrast, the zinc-only preparation failed to protect the cells at any strength tested.
Figure 5B:
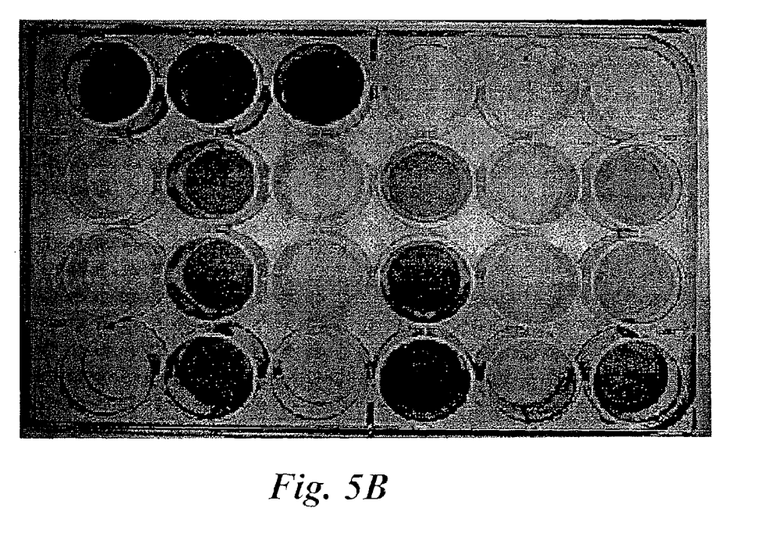
Figure 6A:
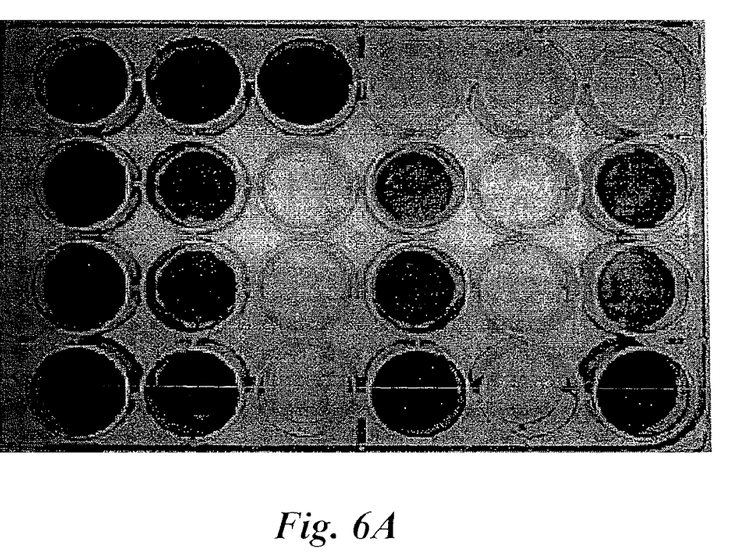
FIG. 6 shows cell protection assay against Rhinovirus. Blue color represents protected cells stained by crystal violet dye. The absence of blue color indicates that all cells were infected and killed by the virus. For Panel A, Antiviral Formulation 1 was used; panel B same as panel A except Antiviral Formulation 2 was used. Similarly, both Antiviral Formulation 1 and Antiviral Formulation 2 were able to completely protect the cells from Rhinovirus infection, even at ⅛ of their original strength. However, zinc-only preparation provided protection only at its ½ strength (i.e., at 0.024% zinc ion concentration), but not at its ¼ and ⅛ strengths.
Figure 6B:
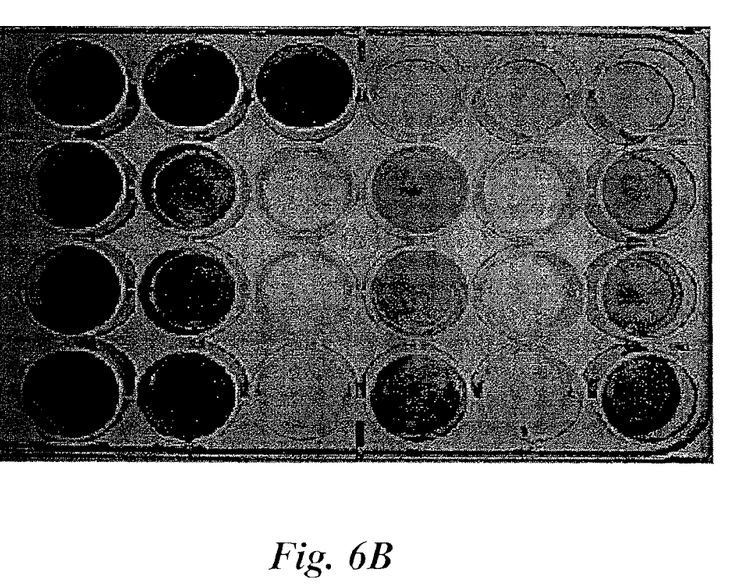

FIGS. 5 and 6 exhibit the color images of the stained well plates. The two LPI-004 formulations against the two viruses are illustrated in the following arrangement:

FIG. 5 shows Antivial Formulation I against influenza B virus (Panel A) and Antiviral Formulation II against influenza B virus (Panel B).

FIG. 6 shows Antiviral Formulation I against rhinovirus (Panel A) and Antiviral Formulation II against rhinovirus First of all, the contrast between the viable cells (blue) and virus-infected cells (colorless) was easily noticeable. It is clearly shown that the two antivial formulations were able to protect the cells from the infections of both human rhinovirus and human Influenza virus. Furthermore, the cells were also protected from infections by both viruses with 2-fold (or at ½ strength) to 8-fold dilution (or at ½ strength) against the same amount of viruses added.

In contrast to the antiviral formulations, the zinc-only preparation failed to show any anti-viral infection activity under the same condition used for LPI-004 formulations (FIG. 5 and FIG. 6) in cell protection assay using influenza B virus and MDCK cell line. Similarly, the zinc-only preparation displayed the anti-viral infection activity only at 2-fold dilution (½ strength), but not at 4-fold (¼ strength) and 8-fold (⅛ strength) dilutions in cell protection assay using rhinovirus and H1-Hela cells. These results indicate that the anti-rhinovirus capability of the zinc-only preparation was highly concentration dependent and appeared to have a narrow effective concentration range.

Data shown in FIGS. 5 and 6 suggest that antiviral formulations of the present invention are efficacious in protecting cells against both human influenza B virus and rhinovirus in a wide concentration range, while the zinc-only preparation is only effective in protecting rhinovirus. In addition, protection by the zinc-only preparation was only observed at a high zinc concentration (0.024% zinc ion).

The zinc-only prepartion was used for comparison because its composition is similar to a commercial cold remedy (Zicam™ nasal spray) and contains the same concentration of zinc ion as in the two exemplary antiviral formulations of the present invention. It appeared that the anti-viral components in addition to zinc formulated in the antiviral formulations of the present invention have not only enhanced the antiviral activity based on the zinc concentration but also broadened the antiviral spectrum to cover human influenza B virus.

The cell protection assay was designed to mimic the situation when a formulation is applied onto human tissue such as a nasal mucosa, other skin or mucous tissues to prevent the tissue from being infected by a pathgenic virus. Since all three test articles (two antiviral formulations and the zinc-only prepartion) are of mucoadhesive and can be expected to form a adhesive layer covering mucous membrane or skin surface, they would form a physical barrier to the invavding virus.

This in vitro assay demonstrates that influenza B virus or rhinovirus could be de-activated upon contact with an antiviral formulation of the present invention even after it has been substantially diluted. Unlike other cell protein assays in which viruses are removed after a brief incubation with cells (usually for 2 h), viruses in this study were kept with cells for 48 h in the presence of the antiviral formulations of the present invention. If cells can be protected under this condition, it would suggested that the antiviral formulations of the present invention may protect cells from virus infection for at least 48 h after it is applied onto the cell surface in vivo. Therefore, the results suggest that the two exemplary formulations of the present invention, when applied as a nasal spray, would likely be capable of preventing cold or flu virus infection through the upper respiratory tract. In summary, both exemplary antiviral formulations of the present invention exhibited cell protection efficacy in vitro against Human Rhinovirus type 15 and Influenza B virus.

Example 5

This example shows a 14 day study to assess a possible irritant effect of daily intranasal administration to male Sprague-Dawley rats.

The purpose of this study was to investigate and compare a possible irritant effect of four formulations following daily intranasal administration of male Sprague-Dawley rats for 14 consecutive days.

Four compositions were tested including three exemplary anti-viral compositions of this invention and one commercially available anti-viral nasal spray product (Zicam Nasal Spray by MATRIXX INITIATIVES, INC.).

Test Article Compositions

| % w/w | Antiviral Formulation I | Antiviral Formulation II | Antiviral Formulation III | Zicam Nasal Spray |
| --- | --- | --- | --- | --- |
| Chitosan chloride (Chimarin ® M-010 by Carmeda AB, Sweden) | 1.5 | | 0.5 | Contains 2% zinc gluconate marketed by Matrixx Initiatives, Inc. |
| Zinc chloride, USP | 0.1 | 0.1 | 0.1 | |
| Benzalkonium chloride, SigmaUltra | 0.02 | 0.02 | 0.02 | |
| Sodium chloride, USP | 0.27 | 0.27 | 0.27 | |
| EUDRAGIT ® E100 | | 0.15 | | |
| NaCl/HCl to adjust pH | 5.6 | 6.2 | 5.6 | |
| Di-ionized water to QS | 100 | 100 | 100 | |

The experimental design was as follows:

| Group | Test Article | Dose Volume (µL/nostril/day) | No. of Animals (Males) |
| --- | --- | --- | --- |
| 1 | LPI-004 (Formulation 1) | 30 | 5 |
| 2 | LPI-004 (Formulation 2) | 30 | 5 |
| 3 | LPI-004 (Formulation 3) | 30 | 5 |
| 4 | Zicam Nasal Spray | 30 | 5 |

At the time of scheduled sacrifice, the animals were euthanized with $CO_2$ followed by exsanguination. Gross necropsy examination was performed on all animals in the study. Tissues and lesions were preserved in neutral buffered 10% formalin at the time of necropsy. Tissue specimens were processed through graded alcohols and a clearing agent, infiltrated and embedded in paraffin, sectioned, and stained with hematoxylin and eosin/phloxine. Sections were prepared at three antero-posterior levels of the nasal cavity. The histologic sections were of adequate size and quality for detection of treatment-related changes. The study protocol, records of gross necropsy observations, and histologic processing records were reviewed at the time of histologic examination.

Histologic examination was performed on sections of nasal cavity from all animals in the study. Histologic observations and a record of tissues examined were entered in a computer-assisted data retrieval system (Starpath, Graham Laboratories, Adkins, Tex.) at the time of histologic examination. The attached tabulation of tissues examined and histologic find ings in those tissues serves as the basis for this narrative report.

All animals survived to the scheduled terminal necropsy. The nasal turbinates of two rats given Antiviral Formulation 2 (Group 2) had mild focal atrophy of the epithelium covering nasal turbinates. The epithelial atrophy in one affected was associated with a mild focal infiltration of lymphocytes and neutrophils, which was recorded as mild focal subacute inflammation. The nasal turbinates of one rat given Antiviral Formulation 3 (Group 3) had minimal focal subacute inflammation.

Subacute inflammation of the nasal tissues is a common incidental finding in laboratory rats, thus the evidence of inflammation seen in this study could not be unequivocally attributed to administration of the test articles. Focal atrophy of the turbinate epithelium is less common, and aroused suspicion of a treatment-related effect. However, the epithelial atrophy that was present in one affected rat was associated with focal subacute inflammation, suggesting the two histologic alterations were causally associated. In addition, the description of the formulations indicates Antiviral Formulation 1 contained 1.5% natural cationic polymer, while Antiviral Formulation 2 contained only 0.5% natural cationic polymer. Presence of turbinate lesions in rats that received the lower dosage level of cationic polymer, as opposed to the higher dosage level, casts doubt on the relationship between turbinate lesions and administration of the test articles. In summary, the results of this example show that administration of the three exemplary antiviral formulations of the present invention or Zicam Nasal Gel to male Sprague-Dawley rats via daily intranasal instillation for 14 consecutive days at dosage levels of 30 µL/nostril/day was associated with no definitive histologic alterations.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An antiviral composition comprising chitosan, a cationic surfactant, and water, wherein
the concentration of chitosan is about 0.1% to about 5% (w/w);
the concentration of cationic surfactant is about 0.01% to about 1% (w/w), wherein the cationic surfactant is benzalkonium chloride; and
the composition is for use in ameliorating an infection by a virus selected from the group consisting of influenzavirus, rhinovirus, adenovirus, coronavirus, parainfluenzavirus, respiratory syncytical virus, and herpes virus, wherein the composition does not contain zinc.

2. The composition of claim 1, wherein the cationic surfactant is benzalkonium chloride.

3. The composition of claim 1, wherein the concentration of chitosan is about 2% (w/w).

4. The composition of claim 1, wherein the concentration of the cationic surfactant is about 0.02% (w/w).

5. The composition of claim 1, wherein the chitosan is in a concentration of 0.1% (w/w), and the benzalkonium chloride is in a concentration of 1% (w/w).

6. The composition of claim 1, wherein the composition optionally comprises one or more members selected from the group consisting of a pH adjusting agent, a pH buffer, a viscosity modifier, an osmotic agent, a flavor, a sweetener, a preservative, an adhesive, and a colorant.

7. The composition of claim 1, further comprising a pharmaceutically acceptable excipient, wherein the composition is formulated for local administration.

8. The composition of claim 1, formulated as a member selected from the group consisting of a solution, a paste, a gel, a suspension, a lotion, a cream, an aerosol, a dressing, a bandage, a lacquer, and an ointment.

9. The composition of claim 1, wherein the composition is for administration as a nasal spray.

10. The composition of claim 1, wherein
the concentration of chitosan is 1.5% (w/w); and
the cationic surfactant is benzalkonium chloride.

11. A method for ameliorating a viral infection caused by a virus selected from the group consisting of influenzavirus, rhinovirus, adenovirus, coronavirus, parainfluenzavirus, respiratory syncytical virus, and herpes virus, said method comprising administering to a subject in need thereof a composition of claim 1.

12. The method of claim 11, wherein the viral infection is caused by an influenza virus.

13. The method of claim 11, wherein
the concentration of chitosan in the composition is 1.5% (w/w); and
the concentration of cationic surfactant is about 0.01% to about 1% (w/w), wherein the cationic surfactant is benzalkonium chloride.

14. The method of claim 13, wherein the cationic surfactant is benzalkonium chloride.

15. The method of claim 11, wherein the concentration of chitosan is about 0.1% (w/w).

16. The method of claim 13, wherein the concentration of the cationic surfactant is about 0.1% (w/w).

* * * * *